US007423068B2

(12) United States Patent
Erickson, Jr. et al.

(10) Patent No.: US 7,423,068 B2
(45) Date of Patent: Sep. 9, 2008

(54) CONTROL OF PARASITIC MITES OF HONEY BEES

(75) Inventors: Eric H. Erickson, Jr., Tucson, AZ (US); Gloria DeGrandi-Hoffman, Tucson, AZ (US); Christian G. Becker, King of Prussia, PA (US); Roy S. Whitson, Fresno, CA (US); Thomas A. Deeby, Tucson, AZ (US)

(73) Assignees: The United States of America as represented by the Secretary of Agriculture, Washington, DC (US); Cerexagri, Inc., King of Prussia, PA (US)

( * ) Notice: Subject to any disclaimer, the term of this patent is extended or adjusted under 35 U.S.C. 154(b) by 456 days.

(21) Appl. No.: 10/944,261

(22) Filed: Sep. 17, 2004

(65) Prior Publication Data

US 2005/0090560 A1  Apr. 28, 2005

Related U.S. Application Data

(63) Continuation of application No. 10/087,161, filed on Feb. 27, 2002, now Pat. No. 6,843,985.

(60) Provisional application No. 60/272,097, filed on Feb. 28, 2001.

(51) Int. Cl.
*A01N 35/02* (2006.01)
*A01N 25/18* (2006.01)
(52) U.S. Cl. ..................... 514/675; 424/405; 424/409; 424/84; 514/964
(58) Field of Classification Search .................. 514/675
See application file for complete search history.

(56) References Cited

U.S. PATENT DOCUMENTS

| | | | |
|---|---|---|---|
| 3,577,515 A | 5/1971 | Vandegaer |
| 4,299,816 A | 11/1981 | Polyakov et al. |
| 4,657,926 A | 4/1987 | Pickett et al. |
| 4,775,534 A | 10/1988 | Bartlett et al. |
| 4,780,479 A | 10/1988 | Pickett et al. |
| 4,867,731 A | 9/1989 | Willard et al. |
| 4,933,371 A | 6/1990 | Hink et al. |
| 5,662,914 A | 9/1997 | Shorey et al. |
| 5,676,958 A | 10/1997 | Emerson et al. |
| 5,719,114 A | 2/1998 | Zocchi et al. |
| 5,750,129 A | 5/1998 | Wakarchuk |
| 5,839,224 A | 11/1998 | Emerson et al. |
| 5,849,317 A | 12/1998 | Shorey et al. |
| 5,948,743 A | 9/1999 | Fonsny et al. |
| 5,990,157 A | 11/1999 | Zocchi et al. |
| 6,037,374 A | 3/2000 | Kochansky et al. |
| 6,051,612 A | 4/2000 | Borden et al. |
| 6,217,891 B1 | 4/2001 | Borden et al. |
| 6,372,239 B1 | 4/2002 | Wu et al. |
| 2001/0014346 A1 | 8/2001 | Watkins |
| 2002/0099101 A1 | 7/2002 | Emerson et al. |
| 2002/0176899 A1 | 11/2002 | Mishima et al. |
| 2002/0193437 A1 | 12/2002 | Nagatsuka et al. |
| 2003/0005484 A1 | 1/2003 | Crandall, Jr. et al. |
| 2003/0044443 A1 | 3/2003 | Erickson et al. |
| 2003/0091657 A1 | 5/2003 | Chiasson |

FOREIGN PATENT DOCUMENTS

| | | |
|---|---|---|
| DE | 4012224 A1 | 10/1991 |
| WO | WO 97/47193 | 12/1997 |
| WO | WO 02/067914 A1 | 9/2002 |

OTHER PUBLICATIONS

Chemical Abstracts 1989:452412 (1989).*
CABA Abstract 87:446 (1987).*
Al-Sa'ad, B.N., Free, J.B. and Howse, P.E., "Adaptation of Worker Honeybees (*Apis mellifera*) to their Alarm Pheromones," Physiological Entomology (1985) 10:1-14.
Boch, R. and Shearer, D.A., "2-Heptanone and 10-Hydroxy-Trans-Dec-2-Enoic Acid in the Mandibular Glands of Worker Honey Bees of Different Ages," Zeitschrift für vergleichende Physiology (1967) 54:1-11.
Boch, R. and Shearer, D.A., "Chemical Releasers of Alarm Behaviour in the Honey-Bee, *Apis mellifera*," J. Insect Physiol. (1971) 17:2277-2285.
Boch, R., Shearer, D.A., and Petrasovits, A., "Efficacies of Two Alarm Substances of the Honey Bee," J. Insect Physiol. (1970) 16:17-24.
Butler, C.G., "Mandibular Gland Pheromone of Worker Honeybees," Nature (1966) 212:530.
Cole, L.K. and Blum, M.S., "Antifungal Properties of the Insect Alarm Pheromones, Citral, 2-Heptanone, and 4-Methyl-3-Heptanone," Mycologia (1975) 67:701-708.
Collins, A.M., Rinderer, T.E., Daly, H.V., Harbo, J.R., and Pesante, D., "Alarm Pheromone Production by Two Honeybee (*Apis mellifera*) Types," Journal of Chemical Ecology (1989) 15(6):1747-1756.
Free, J.B., Pickett, J.A., Ferguson, A.W., Simpkins, J. R., and Smith, M.C., "Repelling Foraging Honeybees with Alarm Pheromones," J. Agric. Sci. Camb. (1985) 105:255-260.
Gallo, J.A.Q., Debeaufort, F. and Voilley, A., "Interactions Between Aroma and Edible Films. 1. Permeability of Methylcellulose and Low-Density Polyethylene Films to Methyl Ketones," J. Agric. Food Chem. (1999) 47 (1):108-113.

(Continued)

*Primary Examiner*—John Pak
(74) *Attorney, Agent, or Firm*—Elizabeth R. Sampson; Margaret A. Connor; John D. Fado

(57) ABSTRACT

The present invention is directed to methods and compositions for use to control parasitic mites of honey bees, particularly *Varroa* mites. In one aspect, the invention is directed to control of parasitic mites of honey bees wherein the active ingredient is a miticidally effective amount of a selected ketone or 1-heptanol, ethyl butyrate, benzaldehyde, heptaldehyde, or d-limonene. In a second aspect, the invention is directed to control of parasitic mites of honey bees wherein the active ingredient is an effective attractant amount of 2-heptanone. The attracted mites are then trapped or otherwise removed from the locus of the bees. The present invention is also directed to methods and compositions which include 2-heptanone to control hive invading pests of honey bees.

6 Claims, No Drawings

OTHER PUBLICATIONS

Huang, Z.-Y., Plettner, E., and Robinson, G.E., "Effects of Social Environment and Worker Mandibular Glands on Endocrine-Mediated Behavioral Development in Honey Bees," J. Comp. Physiol A (1998) 183:143-152.

Keane, S.and Ryan, M.F., "Purification, Characterisation, and Inhibition by Monoterpenes of Acetylcholinesterase from the Waxmoth, *Galleria mellonella* (L.)," Insect Biochemistry and Molecular Biology (1999) 29:1097-1104.

Kraus, B., "Effects of Honey-Bee Alarm Pheromone Compounds on the Behaviour of *Varroa jacobsoni*," Apidologie (1990) 21:127-134.

Lensky, Y. and Cassier, P., "The Alarm Pheromones of Queen and Worker Honey Bees," Bee World (1995) 76(3):119-129.

Naik, D.G., Katke, S. Chawda, S.S., and Thomas, D., "2-Heptanone as a Repellent for *Apis cerana*," J. of Apicultural Research (1997) 36 (3/4):151-154.

Naik, D.G., Banhatt, P., Chadawa, S.S., and Thomas, D., "2-Heptanone as a Repellent for *Apis florea*," Journal of Apicultural Research (2002) 40(1-2):59-61.

Patte, F., Etcheto, M., Marfaing, P., and Laffort, P., "Electroantennogram Stimulus-Response Curves for 59 Odourants in the Honey Bee, *Apis mellifica*," J. Insect Physiol. (1989) 35(9):667-675.

Rieth, J.P., Wilson, W.T. and Levin, M.D., "Repelling Honeybees from Insecticide-Treated Flowers with 2-Heptanone," Journal of Apicultural Research (1986) 25(2):78-84.

Rinderer, T.E., "Sociochemical Alteration of HoneyBee Hoarding Behavior," J. of Chemical Ecology (1982) 8(5):867-871.

Sakamoto, C.H., Soares, A.E.E. and Lopes, J.N.C., "A Comparison of 2-Heptanone Production in Africanized and European Strains of the Honeybee, *Apis mellifera* L.," Journal of Apicultural Research (1990) 29(4):199-205.

Sakamoto, C.H., Soares, A.E.E. and Lopes, J.N.C., "Relationship Between 2-Heptanone and Some Biological and Environmental Variables in *Apis mellifera* L.," Journal of Apicultural Research (1990) 29(4):194-198.

Sanford, M.T., *Apis* Apicultural Information and Issues from IFAS / University of Florida Dept. of Entomology and Nematology (1997) 15(8).

Visscher, P.K., Vetter, R.S. and Robinbson, G.E., "Alarm Pheromone Perception in Honey Bees Is Decreased by Smoke (Hymenoptera: Apidae)," Journal of Insect Behavior (1995) 8(1):11-18.

\* cited by examiner

CONTROL OF PARASITIC MITES OF HONEY BEES

CROSS-REFERENCE TO RELATED APPLICATIONS

This application is a continuation of U.S. patent application Ser. No. 10/087,161, filed Feb. 27, 2002, now U.S. Pat. No. 6,843,985, which claims the benefit of U.S. Provisional Application No. 60/272,097 filed Feb. 28, 2001, now abandoned, and which is related to PCT/US02/05986, filed on Feb. 28, 2002. All prior applications are hereby incorporated by reference in their entirety.

BACKGROUND OF THE INVENTION

1. Field of the Invention

The present invention is directed to methods and compositions to control parasitic mites of honey bees and methods and compositions to control hive invading pests.

2. Description of the Art

Honey bees are necessary to pollinate important agricultural crops and also to produce honey and wax for commercial markets. In the United States, honey bees produce $270 million worth of honey, beeswax, and other hive products and pollinate over $14 billion worth of crops annually.

Parasitic mites are economically important parasites of honey bees which affect honey bee populations worldwide. *Varroa jacobsoni* (Oudemans) (=*V. destructor*) (Acari: Varroidae) are small crab-shaped parasitic mites that are found attached to adult bees or under capped brood cells where they reproduce. In either case, *Varroa* feed on hemolymph by puncturing the exoskeleton of the bee with their mouthparts.

*Varroa* reproduction begins when the adult female enters a brood cell shortly before it is capped. The female must feed on larval hemolymph before she can lay eggs. The *Varroa* eggs eclose under the sealed cell, and the developing mites feed on the bee pupa. The first egg laid by the female *Varroa* develops into a male. Subsequent eggs develop into females that mate with their brother. The mated female mites along with their mother are released from the capped cell when the bee emerges. These mites will hereinafter be referred to as "phoretic mites." The females attach to adult bees between the abdominal segments or between body regions, making them difficult to detect. These are also places from which they can easily feed on the bees' hemolymph. Adult bees serve as intermediate hosts when little or no brood is available and as a means of transport.

*Varroa* mites reduce bee longevity. When infestation levels are high, entire colonies die. *Varroa* are also believed to damage honey bees due to transmission of at least six bee viruses. Spread of *Varroa* mites among colonies can occur due to several factors, including commercial transport of bees and queens, the migratory activities of beekeepers or swarms that may fly long distances.

Maintaining a supply of strong honey bee colonies available for pollination is essential for the sustained production of crops worth more than $14 billion to the U.S. farm economy. Current control measures for *Varroa* include synthetic pesticides. Introducing lipophilic pesticides into honey bee colonies not only contaminates the comb, but opens the possibility of contamination of honey and pollen which are sold to the public.

Presently there is one EPA-registered product under Section 3 of the Federal Insecticide, Fungicide and Rodenticide Act (FIFRA) for control of *Varroa* mites: a plastic strip impregnated with the contact synthetic pyrethroid pesticide fluvalinate (Apistan® strip, Wellmark International). There is also one EPA registered product under Section 3 of FIFRA for suppression of *Varroa* mites: a 65% formic acid gel (Apicure®, Apicure, Inc., believed to be the device of U.S. Pat. No. 6,037,374). In 1999 and 2000 EPA issued an emergency authorization, under Section 18 of FIFRA, for use of the organophosphate coumaphos (CheckMite+™, Bayer Corp.) for control of *Varroa* mites. Formic acid and coumaphos are in EPA toxicity category I which requires the signal word "Danger." Fluvalinate is in EPA toxicity category III which requires a signal word of "Caution." 2-Heptanone is also in toxicity category III.

Of serious concern is the fact that *Varroa* mite resistance to fluvalinate, the most commonly used miticide, has been reported in Europe (Milani, *Apidologie* 30:229-234 (1999); Vedova et al., *Ape Nostra Amica* 19:6-10 (1997)) and in the United States (Elzen et al., *American Bee Journal* 138:674-676 (1998); Elzen et al., *Apidologie* 30:13-18 (1999)). Also, fluvalinate residues have been detected in foundation beeswax used in bee colonies. Resistance to coumaphos is also now being reported. Further, coumaphos, which is also lipophilic, poses the threat of contaminating hive product. The formic acid compositions are effective against tracheal mites but are reported to have limited effectiveness against *Varroa*. Packaging problems have been reported for the formic acid compositions.

To avoid some of the potential problems related to pesticide use in beekeeping, some researchers are selecting strains of bees that tolerate or are resistant to mites. These selection programs take several years, and those colonies that are susceptible to mites will be lost in the interim. Beekeepers need immediate relief from *Varroa* infestations that already exist in their colonies. What is needed are safe and effective ways to control parasitic mites of bees.

Hive invading pests inflict substantial economic losses to beekeepers. One of the most damaging pests to the bee industry is the greater wax moth (*Galleria mellonella*). Currently there is no registered means of controlling this pest. The small hive beetle (*Aethina tumida*), is another destructive pest. There are no known natural enemies of the small hive beetle in the United States. As discussed below, other hive invading pests include ants and the parasitic mite *Tropilaelaps*. What is needed are safe and effective ways to control hive invading pests.

2-Heptanone is a pheromone produced by the mandibular glands of adult worker honey bees, *Apis mellifera* and *Apis cerana* (Vallet et al., *J. Insect Physiol.* 37(11):789-804 (1991); Sakamoto et al., *Journal of Apiculture Research* 29(4):199-205 (1990)), older than 8-10 days. The opening of the mandibular gland is inside the buccal cavity (mouth) of the bee at the base of the mandibles. 2-Heptanone is produced continuously and is universally distributed throughout the bee colony and in the wax. It is believed that the primary function of 2-heptanone in the honey bee hive is that of the principal universal solvent used by the bees to manufacture bees wax comb and propolis (bee glue used to suspend wax combs and plug holes). The bees secrete 2-heptanone while they use their mandibles to masticate (chew) the tiny wax flakes produced by their abdominal wax glands. The wax flakes are formed into uniformly thin wax sheets that are used to build the solid hexagonal wax walls of honey comb cells. Worker bees also gather a variety of plant resins which are solubilized with 2-heptanone and either painted on the surface of the wax honey comb or mixed with wax to produce propolis. A new layer of propolis is painted in brood cells during cleaning after each brood cycle. The net result is that 2-heptanone is incorporated into the structure of the hive interior.

SUMMARY OF THE INVENTION

The present invention is directed to methods and compositions to control parasitic mites of honey bees and methods and compositions to control hive invading pests.

In one embodiment, the invention is directed to miticidal compositions and use thereof to control parasitic mites of honey bees, wherein the active ingredient of the composition is a miticidally effective amount of a compound, which comprises:

(a) a ketone of the structure:

$$CH_3—(CH_2)_x—CO—(CH_2)_y—CH_3$$

wherein y is 0 and x is 0 to 5 or wherein y is 1 or 2 and x is 3 or 2, respectively; or (b) a compound selected from the group consisting of 1-heptanol, ethyl butyrate, benzaldehyde, heptaldehyde, and d-limonene.

In a second embodiment, the invention is directed to attractant compositions and use thereof to control parasitic mites of honey bees, wherein the active ingredient of the composition is an effective attractant amount of 2-heptanone. In this embodiment, mites are exposed to the 2-heptanone, and the attracted mites are then trapped or otherwise removed from the locus of the bees. The composition can be used to detect, survey, monitor, or diagnose mite levels, and control mites by trapping out or otherwise incapacitating attracted mites.

The invention is also directed to methods and compositions comprising 2-heptanone to control hive invading pests. In this embodiment, a selected area, such as a bee hive, bee equipment and the like, is exposed to an effective hive invader-controlling amount of 2-heptanone to prevent hive invading pests from invading the area or to reduce the numbers of pests invading the area.

Currently, there is no economically feasible means to determine if a colony has *Varroa* mites. Since *Varroa* can enter a colony on incoming bees, the mite can be present in a colony at any time. Determining if a colony has *Varroa* is essential for evaluating if control measures are required. Because *Varroa* can enter colonies at any time when bees are foraging, there is not a particular time of year when *Varroa* might be found in colonies. Once *Varroa* establish in a colony, they must be treated to avoid devastating effects on colony populations particularly at certain times of year. The attractant embodiment of the invention provides a simple inexpensive means to monitor the presence of *Varroa* in colonies and provides a pro-active way to reduce the number of mites infesting mite-free colonies.

In accordance with this discovery, it is an object of the invention to provide methods and compositions for control of parasitic mites of honey bees, particularly *Varroa* mites, and to provide methods and compositions for control of hive invading pests.

Another object of the invention is the provision of safe and effective mite control methods and compositions as alternatives to synthetic pesticides (e.g., fluvalinate and coumaphos) or formic acid.

With regard to 2-heptanone, since this compound already exists in bee hives at low levels, there is little chance of toxicity to bees or contamination of hive products.

The miticidal compounds of the invention can be used as a prophylactic to maintain parasitic mite infestation levels below the economic threshold, or reactively to control infestation outbreaks of mites in honey bee colonies. The miticidal compounds can be used alone or in conjunction with other measures incorporated into an Integrated Pest Management Program.

A further object of the invention is to provide miticides for direct control of parasitic mites of honey bees. In one aspect, the invention provides control using 2-heptanone, a compound that naturally occurs in the colony, and thus, the invention is useful to insure the health and vigor of honey bee colonies available for pollination and insure an affordable food supply. In one aspect of the invention, naturally occurring levels of 2-heptanone are augmented to ensure persistence of this volatile compound at miticidal levels.

A still further object of the invention is to provide a means for attracting and trapping *Varroa* mites that are searching for honey bee larvae or to attract and trap mites that have attached to robber bees to prevent the mites from infesting new colonies.

An even further object of the invention is to provide a trapping device using 2-heptanone in an attractant amount to provide inexpensive and effective means to monitor *Varroa* mites while not disrupting honey bee colony behavior or vigor.

It is also an object of the invention to provide a means for controlling hive invading pests.

Other objects and advantages of the invention will become readily apparent from the ensuing description.

DETAILED DESCRIPTION OF THE INVENTION

The present invention is directed to methods and compositions to control parasitic mites of honey bees and methods and compositions to control hive invading pests. In one embodiment, the invention is directed to methods and compositions wherein selected compounds are effective miticides for control of parasitic mites of honey bees. In a second embodiment, the invention is directed to methods and compositions comprising 2-heptanone as an attractant for controlling mites. In another embodiment, 2-heptanone is used for control of hive invading pests.

Definitions: Unless defined otherwise, all technical and scientific terms used herein have the meaning commonly understood by a person skilled in the art to which this invention belongs. The following reference provides one of skill with a general definition of many of the terms used in this invention: *The Hive and The Honeybee*, Ed. Joe M. Graham, Dadant & Sons, Inc., Hamilton, Ill. 1993.

To facilitate understanding of the invention, a number of terms are defined below.

2-Heptanone, $CH_3(CH_2)_4COCH_3$, CAS Registry No. 110-43-0, also known as methyl amyl ketone and methyl pentyl ketone, is a volatile liquid at room temperature [$d_4^{15}$ 0.8197; b.p.$_{760}$ 151.5° C.]. It is soluble in alcohol or ether and very slightly soluble in water. It is available commercially.

Acetone, $CH_3COCH_3$, CAS Registry No. 67-64-1, also known as 2-propanone and dimethyl ketone, is a volatile liquid at room temperature [$d_{25}^{25}$ 0.788; b.p. 56.5° C.]. It is miscible with water, alcohol, dimethylformamide, chloroform, ether, and most oils. It is available commercially.

2-Butanone, $CH_3CH_2COCH_3$, CAS Registry No. 78-93-3, also known as methyl ethyl ketone, is a volatile liquid at room temperature [$d_4^{20}$ 0.805; b.p. 79.6° C.]. It is soluble in about four parts water and miscible with alcohol, ether, and benzene. It is available commercially.

2-Pentanone, $CH_3(CH_2)_2COCH_3$, CAS Registry No. 107-87-9, also known as methyl propyl ketone, is a liquid at room temperature [$d_4^{20}$ 0.809; b.p. 102° C.]. It is almost insoluble in water and is miscible with alcohol or ether. It is available commercially.

2-Hexanone, $CH_3(CH_2)_3COCH_3$, CAS Registry No. 591-78-6 is a liquid at room temperature [b.p. 127° C.]. It is available commercially.

2-Octanone, $CH_3(CH_2)_5COCH_3$, CAS Registry No. 111-13-7, also known as methyl hexyl ketone, is a liquid at room temperature [b.p. 173° C.]. It is available commercially.

3-Heptanone, $CH_3(CH_2)_3COCH_2CH_3$, CAS Registry No. 106-35-4, also known as butyl ethyl ketone, is a liquid at room temperature [b.p. 146-149° C.]. It is available commercially.

4-Heptanone, $CH_3(CH_2)_2CO(CH_2)_2CH_3$, CAS Registry No. 123-19-3, also known as dipropyl ketone, is a liquid at room temperature [b.p. 145° C.]. It is available commercially.

1-Heptanol, $CH_3(CH_2)_5 CH_2OH$, CAS Registry No.111-70-6, also known as n-heptyl alcohol, is a volatile liquid at room temperature [$d_4^{25}$ 0.8187; $b.p._{760}$ 175.8° C.]. It is miscible with alcohol or ether. It is available commercially.

Ethyl butyrate, $CH_3CH_2CH_2COCH_2CH_3$, CAS Registry No. 105-54-4, also known a butanoic acid ethyl ester, butyric acid ethyl ester, and ethyl n-butyrate, is a liquid at room temperature [$d_4^{20}$ 0.879; b.p. 120-121° C.]. It is soluble in about 150 parts water; miscible with alcohol or ether. It is available commercially.

Benzaldehyde, $C_7H_6O$, CAS Registry No. 100-52-7, also known as benzoic aldehyde and artificial essential oil of almond, is a liquid at room temperature [$d_4^{15}$ 1.050; b.p. 179° C.]. It is soluble in about 350 parts water; miscible with alcohol or ether. It is available commercially.

Heptaldehyde, $CH_3(CH_2)_5CHO$, CAS Registry No.111-71-7, also known as heptanal, is a liquid at room temperature [b.p. 153° C.]. It is available commercially.

d-Limonene, $C_{10}H_{16}$, CAS Registry No. 5989-27-5, also known as (R)-(+)-limonene, (+)-4-isopropenyl-1-methyl-1-cyclohexene and (+)-p-mentha-1,8-diene, is a liquid at room temperature [$d_4^{21}$ 0.8402; $b.p._{763}$ 175.5-176° C.]. It is available commercially.

The term "honey bee" refers to members of the Order Hymeoptera, Family Apidae and includes by way of example, the species *Apis mellifera*, and *Apis cerana*.

The term "colony" refers to a community of bees with a single queen, thousands of workers, and brood. During part of the year there are also several hundred drones. The bees live and work together as one family in a hive.

The term "comb" refers to sections of hexagonal bees wax cells built by honey bees and used to rear their brood and store honey and pollen. The cells in each comb are built back-to-back with a common interior wall. The combs are arranged in parallel series.

The term "hive" refers to the cavity/domicile occupied by a honey bee colony. The modern box hive includes a bottom board, cover, and one or more boxes, stacked one above the other. Inside, each box contains a series of movable frames of comb or foundation held in a vertical position a bee space apart.

For the purposes of this invention, a compound is applied for its intended purpose at a level that is greater than the ambient background level. This is described further with reference to 2-heptanone and its use as a miticide, but applies to all embodiments of the invention. As discussed above, 2-heptanone is produced by honey bees, and thus is naturally present in the ambient air of a colony, denoted hereinafter as the "background level." For the purposes of this invention, the effective amount of 2-heptanone to control mites is an amount greater than the ambient background level of 2-heptanone naturally present in the air at the time of exposure. That is, control of parasitic mites is carried out by exposing the target mites to a source of 2-heptanone other than or in addition to the naturally present background level. In one aspect of the invention, naturally occurring levels of 2-heptanone are augmented to ensure persistence of this volatile compound at miticidal levels or at hive invader-controlling levels.

The background amount of 2-heptanone in a hive depends on factors such as time of year, colony size, amount of comb being built, amount of brood in the colony, temperature, and colony demographics (age distribution in the colony). Vallet et al., 1991, supra, estimated the amount of 2-heptanone in a honey bee mandibular gland to be from about 0.1 microliter at emergence to 7 microliters in foraging bees. Determination of the ambient background level of 2-heptanone in the air in a hive (or other locus) of honey bees in a particular set of circumstances can be determined by sampling the air and analyzing for the amount of 2-heptanone per volume of air space using standard GC/MS analysis.

Control of parasitic mites of honey bees refers to any method or means using 2-heptanone or other compound specified above that eliminates or reduces the numbers of mites available to affect honey bees. This includes removing mites from an area where bees are present or may occur; preventing mites from advancing to mite-free areas or reducing the number of mites from advancing to mite-free areas. Control of parasitic mites also includes any method or means using 2-heptanone to attract mites so that they can be trapped or otherwise removed from the locus of the bees.

Control of hive invading pests refers to any method or means using 2-heptanone that eliminates or reduces the numbers of hive invading pests available to affect honey bees.

Dispensing means refers to any means for dispensing controlling amounts of 2-heptanone or other compound specified above. For purposes of this invention, a dispensing means, in its broadest ambit, is defined as any means which both (a) contains or holds unvolatilized compound and (b) releases the compound into the air.

A dispensing means may take several forms. In general, a dispensing means will comprise a means for holding an amount of the compound within a space and for release into the atmosphere. Such dispensing means may be solid or liquid devices or formulations such as monolithic systems, laminated structures, and reservoir systems with or without rate-controlling membranes or formulations. For example, a dispensing means may be as simple as a reservoir or an adsorbent or absorbent material such as cotton or paper, which dispensing means both holds and releases the compound. A preferred dispensing means is a device or formulation which provides controlled release, slow release or sustained release of the compound, as discussed in detail below.

Several types of controlled-release devices exist: those in which the active ingredient forms a core surrounded by an inert diffusion barrier (such devices are frequently referred to as "reservoir" devices); and those in which the active ingredient is dissolved or dispersed in an inert diffusion barrier (such devices are frequently referred to as "monolithic" devices). Each of these devices can obviously exist in a variety of shapes, and can be degradable or non-degradable. Sustained release can also be achieved by a number of other methods such as complexation of the active ingredient, slowly dissolving coatings, erosion, microbial action, use of derivatives or new compounds of reduced solubility or volatility, and the likes.

In monolithic devices, the active ingredient is dispersed throughout (or dissolved in) a substantially inert matrix from which the active ingredient is gradually released in the environment. Non-limiting examples of matrices that have been included in monolithic devices include various gels, waxes, gelatins, natural resins, rubbers, elastomers, synthetic and natural polymers, and the likes. In reservoir devices, several classes of devices exist. One important class includes membranes which are non-porous, homogeneous polymeric films, through which transport occurs by a process of dissolution of the permeating species in the polymer at one interface and diffusion down a gradient in thermodynamic activity. These membranes are usually referred to as solution-diffusion membranes. Another class includes the porous and/or fibrous barriers such as, for example, hollow fibers, porous and/or fibrous materials, in which the active ingredient diffuses mainly by capillary forces. Other less common devices exist where diffusion is taking place under external forces (e.g., gravity, electrical field, vacuum, centrifugal forces, etc.) or mechanical pumping, and the likes.

Formulations such as microencapsulations and emulsions can be used to slow down the release of the active ingredient. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release. Microcapsules are small particles that contain a core material or active ingredient surrounded by a coating or shell. Size typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes. Several processes for preparing microcapsules are described in the literature. Encapsulation processes are often loosely classified as either chemical or mechanical. Examples of chemical processes include but are not limited to complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes include but are not limited to spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Without being limiting, specific exemplary solid controlled release substrates include porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release 2-heptanone or other compound specified above through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of other dispensing means are polymer laminates, polyvinyl chloride pellets, and microcapillaries. Another dispensing means includes using microencapsulation techniques to encapsulate the compound. This includes, for example, encapsulation of the compound in a polyvinyl chloride (PVC)-polyvinyl acetate (PVA) plastic (see for example, Rieth et al., *Journal of Apiculture Research* 25(2):78-84 (1986)). A dispenser may also comprise a release substrate, with the release into the atmosphere controlled by a permeable wall or membrane or by a small opening surrounded by an impermeable wall or membrane or a chemical composition such as a gel composition which holds and releases the compound. Examples of acrylic block controlled release formulations, controlled release strip formulations, and microencapsulation formulations are described in further detail, below and in the Examples.

Liquid forms of release substrates include vegetable and/or mineral oils, preferably containing surface active agents to render the composition readily dispersable in water, such agents include wetting agents, emulsifying agents, dispersing agents, and the like.

Dispensing means for controlled release are described in U.S. Pat. Nos. 5,750,129; 4,775,534; 5,849,317; 6,037,374; 3,577,515, which are incorporated herein by reference in their entirety.

Miticides of the Invention

In this embodiment, the invention is directed to miticidal compositions and use thereof to control parasitic mites of honey bees. The miticidal compounds of the invention comprise:

(a) ketones of the structure:

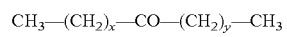

$CH_3-(CH_2)_x-CO-(CH_2)_y-CH_3$ wherein y is 0 and x is 0 to 5 or wherein y is 1 or 2 and x is 3 or 2, respectively; or (b) compounds selected from the group consisting of 1-heptanol, ethyl butyrate, benzaldehyde, heptaldehyde, and d-limonene.

The miticidal compositions contain as the active ingredient one or more of the miticidal compounds of the invention in an effective miticidal amount. This embodiment is useful to control free running or phoretic mites in bee colonies or other areas in which an effective amount can be maintained.

In this aspect, the term control includes treating mites with an effective amount of miticidal compound, that is, an amount which is effective to kill mites, to incapacitate mites such as by disrupting neural or other physiological functions to prevent essential mite functions or reproduction, or render mites impaired sufficiently to be trapped, drowned, isolated, or otherwise removed from an area. An effective miticidal amount is determined as that quantity of compound emitted from a formulation or dispenser holding the compound that is sufficient to accomplish the aforenamed control activities. Treatment may also comprise augmenting naturally occurring levels of 2-heptanone to ensure persistence of this volatile compound at effective levels.

The quantity of miticidal compound must also be insufficient to permanently remove bees from a colony. Tests to determine this can be readily carried out as described in Example 5, below. In our tests of the effects of 2-heptanone on honey bee colony behavior (see Example 5) we found that even very high concentrations tested of 2-heptanone in a colony did not, at any time, cause all bees in the colony to fully and permanently exit the hive. Additionally, our data from colonies and observation hives indicate that effective miticidal concentrations of 2-heptanone do not affect the worker bees in relation to their behavior toward the queen, queen egg laying, or the tendency of bees to remain in the hive and care for the brood.

For control of parasitic mites, particularly *Varroa* mites, in bee colonies, it is preferred that treatment be carried out over a complete brood cycle (21 days for workers or 28 days for drones) and more preferably two or more brood cycles, that is, 42 days or longer.

It is envisioned that the composition of the invention would be useful in killing or incapacitating mites when used with any dispensing means, as described in detail, above. Conveniently, a dispensing means may be left in the hive until all the miticidal compound evaporates.

Examples of dispensing means include a reservoir, controlled release acrylic block, or controlled release strip as described in Examples, below. In any particular instance, the optimum formulation will depend on the mold shape and the active ingredient proportion.

An exemplary acrylic block controlled release formulation is prepared as follows: 5% to 80% of 2-heptanone is mixed with 20% to 95% isobornyl methacrylate and 0% to 30% tripropyleneglycol diacrylate. After the mixing step, benzoyl peroxide is introduced within the mixer at a ratio between 0.05% and 5% and left for homogenization during 30 minutes. Then dimethylparatoluidine (0.05% to 5%) is introduced into the mixer, and the polymerization starts at room temperature. The mixture is introduced into a mold. Polymerization proceeds during several hours and when the temperature of the device is cooled down, the device is removed from the mold.

A more preferred acrylic block formulation comprises: 30% to 70% of 2-heptanone; 30% to 70% of isobornyl methacrylate; 1% to 20% tripropylene diacrylate; 1% to 4% benzoyl peroxide; 0.5% to 2% dimethylparatoluidine. The most preferred formulation comprises: 50% to 60% of 2-heptanone; 30% to 40% of isobornyl methacrylate; 5% to 10% tripropylene diacrylate; 1% to 3% benzoyl peroxide; 0.5% to 2% dimethylparatoluidine.

A controlled release strip formulation can be composed of a solid elastomer matrix impregnated by the compound, e.g., 2-heptanone, and surrounded by a permeable release rate controlling membrane, such as described in U.S. Pat. No. 5,750,129. An exemplary slow release device is as follows: the strip is composed of a polymer sleeve 20 cm long and 5 cm wide in which a polyurethane core containing 60 g 2-heptanone was sealed. The controlled diffusion of 2-heptanone through the membrane can occur over a period of 3 weeks or greater depending on the formulation.

An exemplary slow release oil-gelled 2-heptanone formulation is as follows:

| | |
|---|---|
| 2-heptanone | 10.0% |
| Gelled mineral oil (Versagel ™ C HP) | 90.0% |

Formulation is carried out by quickly mixing both compounds under heat before cooling down the mixture to get a clear gelled mass with a strong 2-heptanone odor. Viscosity as well as release of the final formulation can be modified by using hydrocarbon gels with different properties (e.g., Versagel™ F or M series from Penreco) and different concentrations in 2-heptanone. Versagel™ is a product of Penreco, a Pennzoil/Conoco Partnership, Karns City, Pa. Gel formulations can be dispensed in syringes or guns.

An exemplary slow release gelatin-based 2-heptanone formulation is as follows:

| | |
|---|---|
| 2-heptanone | 23.26% |
| Gelatin (Dynagel) | 3.07% |
| Polyvinylalcohol | 0.29% |
| Water | 73.38% |

An emulsion of 2-heptanone in water was made using polyvinylalcohol as surfactant. The emulsion was then mixed with the gelatin, heated and stirred up to complete dissolution. Upon cooling, the molded formulation gave a compact rubber-like device with slow release properties.

Other compounds and materials may be added to a formulation provided they do not substantially interfere with the miticidal activity of the miticide of the invention. Whether or not an additive substantially interferes with the miticidal activity can be determined by standard test formats, involving direct comparisons of efficacy of the miticidal compound without an additive and the miticidal compound with an additive. Reductions in miticidal activity may be determined with standard statistical analyses.

The dispensing devices can be located as deemed appropriate by the beekeeper for any particular set of circumstances, including next to, within or in contact with the brood nest. For example, without being limiting, one or more dispensing means is placed either on the top board of honey bee colonies or between brood frames. Alternatively, the dispensing means can be placed on the bottom board. Combinations of the foregoing are also contemplated by this invention.

The miticidal compounds of the invention can be used as a prophylactic to maintain parasitic mite infestation levels below the economic threshold, or reactively to control infestation outbreaks of mites in honey bee colonies. The miticidal compounds can be used alone or in conjunction with other measures incorporated into an Integrated Pest Management Program. The compounds may also be useful in controlling certain infectious diseases of honey bees which are carried by mites.

Use of 2-Heptanone As an Attractant to Control Parasitic Mites of Honey Bees

In a second embodiment, control of parasitic mites is carried out using 2-heptanone as an attractant. An effective attractant amount of 2-heptanone is provided in an area to which mites are to be attracted. This includes for example, the brood area which is where mites emerge from cells and search for new hosts, or selected areas where detecting, surveying, monitoring, diagnosing, and/or controlling of mites is desired. Attracted mites respond to 2-heptanone present in air, and they move toward the source of the 2-heptanone. Conveniently, 2-heptanone is dispensed within or adjacent to a trapping means to attract and trap the mites.

Without being bound by theory, it is believed that this mode of action relates to putative host seeking behavior of *Varroa* mites based on the chemistry (2-heptanone content) of honey bee comb containing brood of the appropriate age for parasitism. This discovery has led to feasibility of using 2-heptanone to attract *Varroa* mites in honey bee colonies for the purposes of diagnosis, surveying, monitoring, and control.

As envisioned, a sticky or pitfall trap system utilizing 2-heptanone as the attractant could be used both to diagnose *Varroa* infestation levels, and to reactively trap out mites in honey bee colonies wherein control procedures are warranted. An advantage of the development of a 2-heptanone-based mite trapping system would be reduction of the use of pesticides to diagnose or control *Varroa*. An advantage of the 2-heptanone trapping system is its use as a diagnostic aid, helpful in determining the magnitude of a *Varroa* infestation and thus the need for treatment. A 2-heptanone trapping system may also be useful in diagnosing and controlling other in hive parasites such as the small hive beetle.

The 2-heptanone attractant is also useful pro-actively to prevent or reduce the numbers of *Varroa* infesting previously *Varroa*-free colonies. Colonies become infested when worker bees fly out and rob weakened infested hives. In the infested hive, the mites attach themselves to the robber bees and 'hitchhike' back to the robber bee parent colony where they dismount when near bee brood. A 2-heptanone attractant dispenser would be useful to cause the mites to dismount at such a distance from the brood area of the parent colony that the mites would perish before they could encounter and parasitize bee brood.

An effective attractant amount of 2-heptanone is provided in an area to which mites are to be attracted. An effective attractant amount is defined as that quantity of 2-heptanone that attracts mites to the location of the 2-heptanone at a rate higher than mites are attracted to a location devoid of the added 2-heptanone attractant. An effective attractant amount is determined as the quantity of 2-heptanone emitted from a formulation or dispenser holding 2-heptanone that is sufficient to elicit an attraction response from mites.

It is envisioned that the attractant of the invention would be useful in detecting, surveying, monitoring, diagnosing or controlling mites when used as a lure. A lure includes a dispenser means which contains the attractant. As discussed above, a dispenser means is defined as any means which both (a) contains or holds unvolatilized 2-heptanone and (b) releases 2-heptanone into the air. A dispensing means may take several forms as discussed in detail above, and incorporated herein by reference.

In use in bee colonies, the release device or formulation containing an attractant amount of 2-heptanone can be conveniently placed between brood frames in honey bee colonies. The device attracts mites such as *Varroa* that are searching for honey bee larvae in cells that are just about to be sealed. Traps are used by inserting them into colonies. After a selected period of time, e.g., 48 hours after placing the trap into a colony, it is removed and checked for mites.

Factors such as mite population density, queen states, and environmental factors such as seasonality will influence the response. The amount of 2-heptanone in a particular set of circumstances that will provide release rates within an effective attractant range can be readily determined by a dose response test as described in Example 7, below.

Controlled release of the attractant may also be affected in part through the addition of an extender as known in the art, which will reduce the rate of volatilization of the attractant out of the dispenser.

Other compounds and materials may be added to a formulation, lure, bait or trap provided they do not substantially interfere with the attractancy of the attractant of the invention. Such materials include carriers, extenders, antioxidants, ultraviolet light absorbers, pigments, dyes, fillers, blowing agents, plasticizers, other resin modifying agents and mixtures thereof. Whether or not an additive substantially interferes with the attractant activity, can be determined by standard test formats, involving direct comparisons of efficacy of 2-heptanone without an added compound and 2-heptanone with an added compound. Reductions in attractancy, such as reduced captures of mites in traps baited with the attractant with the additive, may be determined with standard statistical analyses.

The attractant of the invention may be used as a detecting agent, surveying agent, monitoring agent, or control agent for parasitic mites of honey bees. Conveniently, the attractant is dispensed within or adjacent to a trapping means to attract and trap mites. A trapping system includes a trapping means and a dispenser means located within the trapping means which provides an effective amount of 2-heptanone. A trapping means is any device for catching insects, particularly, parasitic mites of honey bees such as *Varroa* mites. These include for example, a sticky or pitfall trap. A sticky board for use to detect infestations of bees by organisms such as mites is described in U.S. Pat. No. 4,867,731.

The attractant of the invention is useful for control of mites when used in concert with other control means, such as by (a) capturing the mites in traps as discussed above, (b) by capturing mites in a trap and killing the attracted mites, for example, by means of a drowning solution or use of a pesticide for mites without endangering bees or contaminating honey and wax.

Use of 2-Heptanone to Control Hive Invading Pests

The invention also relates to the use of 2-heptanone to control hive invading pests from invading or infesting honey bee hives or other selected areas where the presence of hive invaders is to be prevented or reduced.

One of the most damaging pests to the bee industry is the greater wax moth (*Galleria mellonella* Linneaeus (Lepidoptera: Pyralidae)). The moth enters the hive at night and deposits its eggs inside, usually in crevices. The eggs hatch into larvae (caterpillar stage) and burrow into the beeswax comb and destroy the wax combs if not discovered by the beekeeper in time. Also, the business of beekeeping frequently requires the storage of empty hives and combs, particularly over winter. Usually the hives and combs are stored in sheds or warehouses where they are vulnerable to attack by wax moths. The wax moth is viewed by beekeepers as a major pest inflicting substantial economic losses annually, particularly in those states with mild winters. Registrations for pesticides previously used to control wax moths have been withdrawn by EPA. Hence, currently there is no registered means of controlling this pest.

Without being bound by theory, it is believed that the 2-heptanone confuses the signal used by the hive invader, e.g., wax moth, to key on a honey bee colony, and disrupts the invading behavior. Thus, application of a hive invader-controlling amount of 2-heptanone to an area prevents the target hive invader from entering the area or reduces or minimizes the numbers of hive invaders entering the area.

In this embodiment, control is carried out directly using 2-heptanone. An effective hive invader-controlling amount of 2-heptanone is provided in an area where hive invaders are to be controlled, for example, bee hives, empty or stored bee equipment (bee hives with combs), bee colonies, bee brood, stored honey and pollen, wax combs, hives, or wooden hive parts and the like.

In this aspect, the term control means exposing an area to or treating an area with an effective amount of 2-heptanone, that is, an amount which is effective to prevent hive invaders from entering an area where they are to be controlled, or reduces or minimizes the numbers of hive invaders entering the area. An effective hive invader-controlling amount is determined as that quantity of 2-heptanone emitted from a formulation or dispenser holding 2-heptanone that is sufficient to accomplish the aforenamed control activities. The amount of 2-heptanone in a particular set of circumstances or for control of a particular hive invading pest can be determined by a dose response test. Control may be carried out using dispensers discussed in detail above. As described in the Example below, controlled release formulations are effective to control the wax moth in bee hives and wax combs. The devices can be placed on the top board of honey bee colonies, between brood frames, or the bottom board. Combinations of the foregoing are also contemplated by this invention.

The lesser wax moth (*Achroia grisella*), though less destructive than the greater wax moth, has similar habits and can be controlled in the same way as described above for the greater wax moth.

It is within the compass of the invention to control other hive invading pests, including but not limited to, small hive beetles, ants, and *Tropilaelaps*, using the procedures described above.

The small hive beetle (*Aethina tumida*), native to Africa, was accidentally introduced into the United States in the early 1990's. Since then it has spread to several eastern states and continues to expand its range. This destructive pest chews wax combs and feeds on the honey stored therein, rapidly reducing the colony to a soggy, sticky mess. There are no known natural enemies of the small hive beetle in the United States. One organophosphate insecticide (coumaphos) is registered for control.

Several species of ants (Formicidae) invade honey bee colonies and interact with them in many ways. Some consume the wood the hive is made of. Others consume honey, pollen or brood, and even adult bees. They weaken and destroy colonies. The need to control ants in honey bee colonies is widely recognized, however, there are few effective treatments.

The parasitic mite *Tropilaelaps* (*Tropilaelaps clarae*) is currently found throughout Southeast Asia, and parts of Africa, China, India, eastern Europe. It is anticipated that this species will be accidentally introduced into the United States within the next 5 to 15 years. These relatively large mites feed on bee brood. Damage to colonies is usually rapid and severe following initial infestation. Effective treatment is currently limited to cumbersome management strategies.

EXAMPLES

The following examples are intended only to further illustrate the invention and are not intended to limit the scope of the invention which is defined by the claims.

Example 1

This example describes petri dish bioassays for miticidal activity.

2-Heptanone was tested for miticidal activity in two separate sets of bioassays. In the petri dish bioassays we exposed free-running adult mites to volatiles from 2-heptanone either in pure form or in an acrylic block dispenser (as described in a further experiment, below) and measured mortality over time. Mites were placed in petri dishes (5-10 mites/dish, 4 dishes per treatment and 4 dishes for controls) that were lined on the bottom with damp tissue paper covered with Parafilm®. Holes were punched in the Parafilm® using an insect pin to create a humid environment in the petri dish. A piece of filter paper the same size as the petri dish was placed on top of the Parafilm® sheet. In the first petri dish bioassay, 40 µl of pure 2-heptanone was placed on a piece of filter paper on the lid of the petri dish (treatment dishes). The Control dishes were set up as described above but nothing was added to the piece of filter paper fastened to the lid of the petri dish. The petri dishes were placed in separate incubators for treatments and Controls. Incubator temperatures were maintained at 33-34.4° C. In less than 2 hrs., all the mites were dead in the dishes containing the 2-heptanone compared with 0% mortality in the controls. In the second bioassay 0.1 g of a 30% concentration of 2-heptanone in acrylic block made as in Example 6 was placed in a plastic weighing boat in the center of petri dishes prepared as described above. Control petri dishes were prepared identically to those containing the acrylic block, but the weighing boat in the center of the dish was empty. In the petri dishes containing the 2-heptanone in the acrylic block dispenser, 90% of the mites were dead in 4 hrs. compared with 6% mortality in the controls.

In another series of tests, 2-heptanone, 98+% (Sigrma-Aldrich); 3-heptanone (Fluka Chemika); 4-heptanone (Fluka Chemika); 2-hexanone; 2-octanone, 98% (Aldrich Chemical Co.); 1-heptanol (Fluka Chemika, 99.5% GC), and heptaldehyde, 95% (Aldrich Chemical Co.) were tested in petri dish bioassays wherein free-running adult mites were exposed to 40 µl of pure compound placed on filter paper as described above. The test conditions and Controls were as described above. The results are shown in Table 1, below.

TABLE 1

Miticidal Activity in Petri Dish Bioassays

| Treatment | Exposure Time (hrs) | % Mortality Treatment | Control |
|---|---|---|---|
| 2-Heptanone | 1 | 100 | 0 |
|  | 2 | 93 | 0 |
| 3-Heptanone | 2 | 100 | 0 |
| 4-Heptanone | 1 | 100 | 0 |
|  | 2 | 100 | 0 |
| 2-Hexanone | 1 | 100 | 0 |
| 2-Octanone | 1 | 100 | 0 |
| 1-Heptanol | 1 | 65 | 0 |
|  | 2 | 75 | 10.5 |
| Heptaldehyde | 1 | 100 | 0 |
|  | 2 | 100 | 10.5 |

In another series of tests, acetone (Mallinckrodt); 2-butanone, 99.5+%, HPLC grade (Aldrich, Chemical Co.); ethyl butyrate, 99% (Aldrich Chemical Co.); benzaldehyde (Sigma Chemical Co.), and d-limonene (Sigma Chemical Co. Catalog No. 12129) were tested in petri dish bioassays wherein free-running adult mites were exposed to 40 µl of pure compound placed on filter paper as described above. The test conditions and Controls were as described above. The results in Table 2, below.

TABLE 2

Miticidal Activity in Petri Dish Bioassays

| Treatment | Exposure Time (hrs) | Average % Mortality ± S.E.* Treatment | Control |
|---|---|---|---|
| Acetone | 1 | 48 ± 8.65 | 0 |
|  | 2 | 81.2 ± 12.0 | 12.5 ± 7.22 |
| 2-Butanone | 1 | 87.5 ± 7.22 | 0 |
|  | 2 | 77.3 ± 15.6 | 12.5 ± 7.22 |
| Ethyl Butyrate | 1 | 81.2 ± 12.0 | 0 |
|  | 2 | 81.2 ± 12.0 | 0 |
| Benzaldehyde | 1 | 55 ± 12.6 | 0 |
|  | 2 | 100 | 0 |
| d-Limonene | 1 | 5.0 ± 5.0 | 0 |
|  | 2 | 55.0 ± 9.57 | 0 |

*S.E. is ± 0 unless otherwise noted

Example 2

In these experiments 2-heptanone was tested for miticidal activity in colonies.

This set of bioassays was conducted in 5-frame colonies. We tested miticidal activity of 30% concentration 2-heptanone in an acrylic block dispenser. Four colonies were established for each of the following treatments: 2-heptanone, Apistan® (a commercially available miticide for control of *Varroa*), and no treatment (i.e., Controls). Before each treatment, counts were made of the number of mites that dropped on to Dewill® *Varroa* Mite Detector Inserts (hereinafter denoted as "sticky boards") placed at the bottom of colonies for one week (pre-treatment counts). A new sticky board then was inserted at the bottom of each colony, and either a single acrylic block dispenser with 30% 2-heptanone made as in Example 6 (surface area=28.3 cm$^2$) or a single Apistan® strip was placed between the frames. The Controls comprised no treatment. The number of mites on the sticky boards was counted weekly for 3-4 weeks afterwards (treatment interval). New sticky boards were inserted at the beginning of each week. At the end of the test period, the 2-heptanone and Apistan® were removed, and a new sticky board was inserted on the bottom of the colonies. A new Apistan® strip then was placed in the colonies to kill any remaining mites (post-treatment interval). The number of mites on the sticky board was counted after the colony was exposed to the new Apistan® strip for one week. The % Reduction in the *Varroa* Population was estimated by summing all the mites counted on the sticky board during the 3 or 4 week treatment interval and dividing it by the total number of mites counted for the colony during both the treatment and post-treatment intervals. The results of two bioassays that followed this protocol are shown below in Table 3.

TABLE 3

The percentage of Varroa mite killed by exposure to 2-heptanone, fluvalinate (Apistan ®) or no treatment (Control)

| Treatment | Trial | Sample Size (# of colonies) | % Reduction in Varroa Mite Population ± S.E. |
|---|---|---|---|
| 2-Heptanone | 1 | 4 | 61.8 ± 8.5 a |
| Apistan ® | 1 | 4 | 94.1 ± 1.5 b |
| Control | 1 | 4 | 42.2 ± 7.0 c |
| 2-Heptanone | 2 | 3 | 73.6 ± 13.7 a |
| Apistan ® | 2 | 4 | 94.1 ± 1.2 b |
| Control | 2 | 4 | 43.6 ± 4.2 c |

In Trial-1, 2-heptanone was less effective then Apistan® but more effective than the Control according to a Fishers Least Significant difference test (critical value=20.5 for α=0.05). When we removed the acrylic strips from the colony after three weeks, we could still detect the odor of 2-heptanone. We repeated the test with new colonies, and in this trial (Trial-2) left the 2-heptanone and Apistan® strips in the colony for 4 weeks. We then placed the post-treatment Apistan® strips in the colonies. In Trial-2, 2-heptanone was not as effective as Apistan® but was more effective than the Control according to a Fishers Least Significant difference test (critical value=5.6 for α=0.05).

This test (Trial 3) was carried out in 5-frame colonies as described above except for the following changes. In this test, 2-heptanone was released using a controlled release strip as described in U.S. Pat. No. 5,750,129. In brief, the controlled release strip was composed of a polymer sleeve 20 cm long and 5 cm wide in which a polyurethane core containing 60 g 2-heptanone was sealed. The 2-heptanone strip was placed on the top of the frame (top bar). The controlled diffusion of 2-heptanone through the membrane occurred over a period of 3 weeks. A new 2-heptanone controlled release strip was placed on the top bar after 3 weeks. The Apistan® strip was placed between the frames as described above. The Control comprised no treatment. The results are shown in the Table 4, below.

TABLE 4

The percentage of Varroa mite killed by exposure to 2-heptanone, fluvalinate (Apistan ®) or no treatment (Control)

| Treatment | Sample Size (# of colonies) | % Reduction in Varroa Mite Population ± S.E. |
|---|---|---|
| 2-Heptanone | 4 | 87.05 ± 4.4 a |
| Apistan ® | 4 | 92.40 ± 3.3 a |
| Control | 4 | 69.35 ± 4.8 b |

F Value 9.65, P Value 0.008
Critical Value = 13.5; α = 0.05

Example 3

The following example describes tests to determine the influence of 2-heptanone on honey bee colony behavior.

Tests were conducted with 2-heptanone in pure form and in a 30% concentration in acrylic block made as in Example 6 to determine its effects on the honey bee (*Apis mellifera* L.) colony behavior. A two-frame observation hive (the hive had one frame on the bottom with adult worker bees and brood and a top frame with adult worker bees and honey) with a laying queen was used for the study. When we placed a piece of filter paper containing 40 µl of pure 2-heptanone in the observation colony, all the bees moved off of the frame and began to fan (i.e., move their wings up and down) vigorously. Within 4 hours the 2-heptanone had evaporated, and the bees returned to the frame, and the fanning stopped.

To test the effects of 2-heptanone in acrylic blocks, we again conducted studies using two frame observation hives arranged as described above. For one week prior to inserting the acrylic blocks, we measured queen ovipositions, and the number of workers bees leaving the hive per 5-minute interval in four observation colonies. We also counted the number of workers in a court surrounding the queen once during the 5-minute interval. We then added one acrylic block dispenser with a surface area of 8.04 cm$^2$ containing a 30% concentration of 2-heptanone. Two observation colonies contained the acrylic blocks with 2-heptanone and two did not. The latter served as Controls.

2-Heptanone had no immediate effect on the bees on the frames when we inserted it into the observation hive. The aroma of 2-heptanone could be detected emanating from the colony, so we knew it was being released in the colony. The number of worker bees forming the queen's court and the number of ovipositions per 5-minute interval did not differ in the treatment colonies after 2-heptanone was added to the hive (Table 5). Foraging activity was slightly higher after 2-heptanone was added as determined by a Student's t-test.

TABLE 5

The average number of worker bees in the court surrounding the queen, ovipositions by the queen, and foragers leaving the hive per 5-minute interval in colonies before and after 2-heptanone was added to the hive. Control colonies did not have 2-heptanone added at any time during the study.

| Colony Type | Pretreatment | | | Post-Treatment | | |
|---|---|---|---|---|---|---|
| | Workers in court | Ovipositions | Foragers leaving | Workers in court | Ovipositions | Foragers leaving |
| Control | 12.7 | 2.8 | 18.3 | 9.3 | 3.5 | 18.3 |
| 2-Heptanone | 10.2 | 5.3 | 16.1 | 10.2 | 5.3 | 23.6* |

*Indicate means that are significantly different at p = 0.05 as determined by a Students t-test.

Example 4

This experiment shows the Minimum Level Treatment Effectiveness.

Determination of the minimum amount of 2-heptanone effective in mite mortality in our bioassay was performed according to the following procedure: 3 Kimwipes® were placed on the bottom of petri dishes and slightly moistened with water using a disposable 1 ml pipette. A cut section of Parafilm® M was placed over the moistened Kimwipes® and stretched up and over the outer edge of the petri dish bottom. The Parafilm® stretched over the Kimwipes® was then repeatedly pierced with a small dissecting insect pin to create a humid environment in the petri dish. A single Whatman® Filter paper (9.0 cm) was placed on top of the pierced Parafilm® area and pushed down to create space between the filter paper and the petri dish lid. Six to eight mites and two bee larvae were placed on top of the filter paper in each petri dish. A small strip of filter paper was taped to the inside top of each petri dish. Four groups of two petri dishes were labeled according to the type of treatment. The treatments were: 1 µL 2-heptanone; 5 µL 2-heptanone; 10 µL 2-heptanone; and Control (no treatment). All eight dishes were then placed in incubators set to maintain a temperature of 33-34.4° C. Our results were as follows:

TABLE 6

Threshold Concentration for 2-Heptanone (Low)

| Treatment | Dish # | % Mortality 1 hour | % Mortality 17.5 hours | % Mortality 25.5 hours | % Mortality 40.5 hours |
|---|---|---|---|---|---|
| Control | 1 | 0% | 20% | 25% | 25% |
| | 2 | 0% | 25% | 25% | 25% |
| 1 µL | 1 | 16% | 33% | 66% | 66% |
| | 2 | 0% | 0% | 50% | 50% |
| 5 µL | 1 | 100% | 100% | 100% | 100% |
| | 2 | 17% | 33% | 33% | 68% |
| 10 µL | 1 | 17% | 66% | 66% | 66% |
| | 2 | 0% | 40% | 50% | 60% |

These results indicate that at higher concentrations, 2-heptanone has a knockdown action on the mites. In our 1-hour observations we thought the mites were dead but they were merely inanimate. Over time as 2-heptanone evaporated the mites became active again.

In our second bioassay, the same protocol was applied; however we sought to investigate if lower amounts of 2-heptanone could be as effective. In this trial, amounts of 0.5 and 1 µL of 2-heptanone were used. After 17.5 hours exposure to 2-heptanone, our results were as follows:

TABLE 7

Threshold Concentration for 2-Heptanone (Low)

| Treatment | Dish # | # of Dead Mites/ Total Mites | % Mortality |
|---|---|---|---|
| Control | 1 | 1/5 | 20% |
| | 2 | 3/5 | 60% |
| | 3 | 0/6 | 0% |
| | 4 | 1/6 | 17% |
| 0.5 µL 2-heptanone | 1 | 1/6 | 17% |
| | 2 | 1/5 | 20% |
| | 3 | 2/6 | 34% |
| | 4 | 0/5 | 0% |
| 1 µL 2-heptanone | 1 | 3/6 | 50% |
| | 2 | 0/5 | 0% |
| | 3 | 1/4 | 25% |
| | 4 | 1/5 | 20% |

There was no significant difference in the average % mortality among the different treatments as determined by an F-test (F=0.12, df=2,9; p>0.05).

Conclusion:

Based upon our results, we believe that 1 µL is the minimum amount of 2-heptanone that will cause mite mortality. This corresponds to a concentration of 1800 ppm v/v or 0.18%.

Example 5

This experiment examines the maximum levels of 2-heptanone without negatively impacting bee behavior.

A test was conducted with 2-heptanone in pure form to determine its effects on honey bee (*Apis mellifera* L.) colony behavior and ascertain if there was a maximum dose of 2 heptanone that could induce a colony to leave their hive. Two full sized frames were taken from a colony in our local apiary and placed inside a two-frame observation hive having a total volume of 8565 cm$^3$. These two frames contained adult worker bees only and were queenless. A 2-day period when no testing occurred was included to allow for colony adjustment to the new dwellings. The observation hive was set up inside a greenhouse with a 2.5 cm tube connected from the side of the observation hive to the side wall of the greenhouse. This tube served as an exit and entrance for the workers.

We fastened a strip of filter paper measuring 7.6 cm by 2.5 cm to the top inside frame of the observation colony with a thumbtack and applied an initial 100 µL of pure 2-heptanone to the filter paper and observed worker behavior. Subsequent applications of 40 µL of 2-heptanone were applied every 4 minutes with observations of worker behavior documented. Ambient temperature at the time of the observations was 23° C.

After 24 minutes exposure time, we removed the initial filter paper and replaced it with a new filter paper strip measuring 5 cm by 15 cm and placed a new amount of 340 µL of 2-heptanone and resumed the application pattern of 40 µL ever 4 minutes until 460 µL was reached. At this point, we again replaced the filter paper with a new filter paper strip measuring 5 cm by 15 cm and saturated this final piece with 460 µL of 2-heptanone.

Our experiment ended when 500 µL of pure 2-heptanone was the total amount on our filter paper. Concentration of 500 µL of 2-heptanone in the two-frame observation hive was calculated to be 2700 ppm v/v or 0.27%.

Results

With each 40 µL addition at the various intervals, the colony's initial reaction was movement away from the source of 2-heptanone (filter paper piece). However, after a period of 3-4 minutes, workers returned and began to walk on the strip and in the immediate area of the strip. When strips with highest concentration were placed within the colony (100 µL, 340 µL, 460 µL), workers responded by running throughout the observation hive or moving towards the exit tube and exiting the observation hive to the outside. At no time however, did all bees fully or permanently exit the observation hive. Many of the workers filtered towards the exit tube, but never were there more than 100-150 bees outside the exit of the observation colony.

We believe that with each additional dosage of 2-heptanone, worker bees became acclimated to the 2-heptanone.

Example 6

This example shows how the acrylic blocks described above were made.

Blocks having the following composition were made:

| | |
|---|---|
| isobornyl methacrylate: | 50% |
| tripropyleneglycol diacrylate | 6% |
| 2-heptanone: | 44% |

Polymerization was triggered with 2.9% benzoyl peroxide and 1.1% dimethylparatoluidine. Each block weighed approximately 30 grams (Diam. 60 mm, Height 10 mm). The blocks were molded in an aluminum cup.

However, it was found, because of a packaging problem, that the blocks lost some active ingredient during transportation and had only 30% 2-heptanone. To avoid any further loss of active ingredient, the unused samples were stored at all times in a refrigerator at 4° C. The value of 30% 2-heptanone was kept for further processing of the data. The rate at which 2-heptanone was released from the blocks was measured. The experimental procedure consisted in weighing the acrylic blocks left in their aluminum mold at regular intervals. The blocks were kept in an incubator set at 34° C. (temperature of the center of the brood nest in a honey bee hive). It is noteworthy that the incubator is not air tight and that the incubator glass door had to be opened to retrieve the sample to be weighed. An Isotemp Incubator from Fisher Scientific was used. The incubator has a measured volume of 71 liters. The samples were monitored for 44 days.

The release rate data at 34° C. (Table 8) shows an initial strong burst of 2-heptanone which rapidly decreases in the first 10 days to stabilize at a lower but steadier release for the following 35 days.

TABLE 8

| Day | % 2-Heptanone loss (initial conc. 30%) | Daily release in percentage |
|---|---|---|
| 0 | 0 | 0 |
| 1 | 29.13 | 29.13 |
| 2 | 38.76 | 9.63 |
| 3 | 49.04 | 10.28 |
| 4 | 55.72 | 6.68 |
| 7 | 68.85 | 4.38 |
| 8 | 71.82 | 2.97 |
| 9 | 74.7 | 2.88 |
| 10 | 76.09 | 1.39 |
| 11 | 77.88 | 1.79 |
| 14 | 82.31 | 1.48 |
| 15 | 83.43 | 1.12 |
| 16 | 84.39 | 0.96 |
| 18 | 86.24 | 0.92 |
| 21 | 88.43 | 0.73 |
| 24 | 89.98 | 0.52 |
| 30 | 92.36 | 0.4 |
| 44 | 95.21 | 0.2 |

Example 7

These experiments evaluate 2-heptanone as an Attractant for *Varroa* Mites.

We conducted bioassays to determine if 2-heptanone attracts *Varroa* mites. In the first bioassay, we exposed free-running adult mites to volatiles from a 20% 2-heptanone in a gel formulation. Mites were placed in petri dishes (5-10 mites/dish, 4 dishes per treatment and 4 dishes for controls) that were lined on the bottom with damp tissue paper covered with Parafilm®. Holes were punched in the Parafilm® using an insect pin to create a humid environment in the petri dish. A piece of filter paper the same size as the petri dish was placed on top of the Parafilm® sheet. 40 µL of 20% 2-heptanone in a gel formulation was added to a weighing boat located in the center of the petri dish. Control dishes were set up as described above with empty weighing boats in the center. Within 24 hours 27.3% of the mites were found in the gel formulation of 2-heptanone located in the weighing boat in the center of the petri dish. No mites were found in the weighing boat in the Control dish. The bioassay was repeated using the same procedure as described above. In the second replicate, 16.7% of the mites were found in the gel formulation of 2-heptanone located in the weighing boat in the center of the petri dish and again 0% were found in the weighing boats of the Control dishes.

In a second test to determine if 2-heptanone is an attractant, a *Varroa* trapping device was placed in a *Varroa*-infested 9-frame colony for 48 hrs. The device was constructed by placing a 2.54 $cm^2$ piece of Dewill® *Varroa* Mite Detector Insert coated with a 20% concentration of 2-heptanone in a gel formulation and covered with a 0.63 cm (0.25 inch) wire mesh. A wire was placed through the top of the trap so that the trap dangled between the frames in the colony. The device was placed between frames containing brood. After 48 hrs, several hundred *Varroa* mites were found stuck in the gel on the trap behind the wire mesh.

A third bioassay to test for attractiveness of 2-heptanone to *Varroa* was conducted in petri dishes with a diameter of 13.97 cm and a volume of 76.64 $cm^3$. The dishes were prepared as described previously in the first bioassay of this Example using 20% gel formulation of 2-heptanone. However, the petri dishes for this bioassay were modified by drilling a hole 1.6 cm in diameter into the center of the dish. This hole was large enough to fit a 1.5 mL Eppendorf® tube which would serve as the dispenser for the 2-heptanone. The lid of each petri dish was labeled in a "bulls eye" fashion with concentric circles at 1.27 cm increments from the center where the Eppendorf® tube was located. The maximum distance from the center was 6.35 cm. The Eppendorf® tube is considered the target. In the treatment dishes, 0.04 g of 2-heptanone in acrylic block formulation (30% concentration) was placed in the Eppendorf® tube and covered with a small amount of sterile cotton. Control dishes were prepared in the same manner as the treatment dishes but the Eppendorf® tubes contained only cotton. Mites (4-5 per dish) were placed in each dish in the area furthest from the center where the Eppendorf® tube was located.

After the dishes were prepared a square section of mosquito netting large enough to cover the top of the petri dish was placed over the dish and secured with a rubber band. The mosquito netting was used instead of a lid on the dish. The mesh of the netting was wide enough to allow the 2-heptanone to volatilize, but prevented the mites from escaping. The marked lids were placed on top of the dishes every 30 minutes to document mite movement. After the measurements were made, the lids were immediately removed. The petri dishes were observed in 30 minute increments, and the movement of the mites towards or away from the center Eppendorf® tube was documented by counting the number of mites in each concentric circle.

After 1 hr significantly more mites ($p<0.05$) in the treatment dishes were closer to the target (1.3 cm from the Eppendorf® tube with the 2-heptanone) than the mites in the Control plate (Table 9). More mites were in the 1.3 cm region throughout the bioassay, but the differences were not significant at the $\alpha=0.05$ level. Mites were found in the Eppendorf® tube target in both treatments and Controls, but remained in neither.

TABLE 9

Percentages of Varroa mites various distances from a target source containing 2-heptanone (30% concentration in acrylic block delivery system) over a 4 hr. observation period.

| Treatment | Exposure Time (hrs.) | % of Varroa Various Distances from Target Source (cm) | | | | | |
|---|---|---|---|---|---|---|---|
| | | 6.3 | 5.1 | 3.8 | 2.5 | 1.3 | Target |
| 2-Heptanone | 1 | 17.5 | 16.2* | 25.0 | 7.5 | 27.5* | 0 |
| Control | 1 | 18.7 | 50.6* | 20.0 | 15.0 | 5.0* | 2.5 |
| 2-Heptanone | 2 | 10.0 | 15.0 | 12.5 | 20.0 | 32.5 | 7.5 |
| Control | 2 | 22.5 | 39.4 | 10.0 | 8.2 | 17.5 | 5.0 |
| 2-Heptanone | 3 | 7.5 | 12.5 | 22.5 | 10.6 | 45.6 | 3.1 |
| Control | 3 | 10.6 | 32.5 | 18.7 | 13.1 | 19.4 | 0 |
| 2-Heptanone | 4 | 5.5 | 18.8 | 20.0 | 13.3 | 42.2 | 0 |
| Control | 4 | 10.0 | 36.7 | 20.8 | 7.5 | 25.8 | 0 |

*Means are significantly different between treatments and Controls as determined by a t-test at the $\alpha = 0.05$ level.

A fourth test of attractiveness was conducted in the petri dishes that were prepared as described above. In this test 0.06 g of 2-heptanone (30% concentration in acrylic block delivery system) was placed in the center target of the treatment plates. Control plates contained an empty Eppendorf® tube. The mites were placed 3.17 cm from the target. The mites could move closer or farther away from the target. Two treatment and two Control plates with 5 mites each were observed. During the 4 hr. observation period, significantly more mites moved within 1.27 cm of the target (38.4%) compared to the Controls (6.2%) (t=4.01, p=0.0015), and 9.1% moved into the target in the treatment plates compared with 0.0% for the Controls.

Example 8

The following example describes use of 2-heptanone to control the hive invading pest, the wax moth (*Galleria mellonella*).

We conducted an experiment where we stored five frames with drawn comb in a nucleus colony box without bees present. In three nucleus colony boxes we placed 1, 2 or 3 strips containing 60 grams of 2-heptanone in a slow release formulation. In a fourth nucleus colony box we placed no 2-heptanone. Within 2 weeks after the start of the experiment, the equipment without 2-heptanone had wax moth adults present between the frames. The adults probably were laying eggs. After 5 weeks, the equipment without 2-heptanone was totally infested with wax moth. There still was no wax moth in any equipment containing 2-heptanone.

It is understood that the foregoing detailed description is given merely by way of illustration and that modification and variations may be made within, without departing from the spirit and scope of the invention. All publications and patents cited herein are hereby incorporated by reference in their entirety.

What is claimed is:

1. A method of controlling parasitic mites of honey bees, which comprises exposing parasitic mites to a miticidally effective amount of a compound selected from the group consisting of 2-butanone, 2-pentanone, 2-hexanone, 2-octanone, 4-heptanone, and 3-heptanone;
   wherein said miticidal amount is effective to kill mites, to incapacitate mites by disrupting neural or other physiological functions to prevent essential mite functions or reproduction, or to render mites impaired sufficiently to be trapped, drowned, isolated, otherwise removed from an area.

2. The method of claim 1 wherein said parasitic mites are *Varroa* mites.

3. The method of claim 1 wherein said controlling is carried out by placing said effective amount of said miticidal compound inside a honey bee hive so that vapors of said compound are distributed in the hive.

4. The method of claim 1 wherein said effective amount of said miticidal compound is dispensed by a dispensing means comprising a device or formulation which provides controlled release, slow release or sustained release of said compound.

5. The method of claim 4 wherein said parasitic mites are exposed to an effective amount of said miticidal compound for one or more brood cycles.

6. The method of claim 5 wherein said parasitic mites are exposed to an effective amount of said miticidal compound for two or more brood cycles.

* * * * *